(12) United States Patent
Blanchard et al.

(10) Patent No.: US 12,426,617 B2
(45) Date of Patent: Sep. 30, 2025

(54) INFANT FORMULA

(71) Applicant: SOCIETE DES PRODUITS NESTLE S.A., Vevey (CH)

(72) Inventors: Carine Blanchard, Le Mont-sur-Lausanne (CH); Sebastien Holvoet, Montpreveyres (CH)

(73) Assignee: Societe des Produits Nestle S.A., Vevey (CH)

( * ) Notice: Subject to any disclaimer, the term of this patent is extended or adjusted under 35 U.S.C. 154(b) by 589 days.

(21) Appl. No.: 17/758,160

(22) PCT Filed: Dec. 28, 2020

(86) PCT No.: PCT/EP2020/087901
§ 371 (c)(1),
(2) Date: Jun. 29, 2022

(87) PCT Pub. No.: WO2021/136751
PCT Pub. Date: Jul. 8, 2021

(65) Prior Publication Data
US 2023/0026618 A1 Jan. 26, 2023

(30) Foreign Application Priority Data
Dec. 30, 2019 (EP) .................................. 19219957

(51) Int. Cl.
| A23L 33/00 | (2016.01) |
| A23L 33/115 | (2016.01) |
| A23L 33/125 | (2016.01) |
| A23L 33/17 | (2016.01) |
| A61P 37/00 | (2006.01) |

(52) U.S. Cl.
CPC ............. *A23L 33/40* (2016.08); *A23L 33/115* (2016.08); *A23L 33/125* (2016.08); *A23L 33/17* (2016.08); *A61P 37/00* (2018.01)

(58) Field of Classification Search
None
See application file for complete search history.

(56) References Cited

U.S. PATENT DOCUMENTS

| 2012/0171166 A1 | 7/2012 | Chow et al. |
| 2013/0243797 A1 | 9/2013 | Sprenger |
| 2015/0335052 A1 | 11/2015 | Sprenger et al. |
| 2016/0044947 A1 | 2/2016 | Destaillats et al. |
| 2016/0296541 A1 | 10/2016 | Sangild |
| 2016/0296543 A1 | 10/2016 | Brassart et al. |
| 2017/0231261 A1 | 8/2017 | Thakkar et al. |
| 2018/0110253 A1 | 4/2018 | Sprenger et al. |
| 2018/0228195 A1 | 8/2018 | Thakkar |

FOREIGN PATENT DOCUMENTS

| CN | 108471793 A | 8/2018 | |
| WO | 2016046294 | 3/2016 | |
| WO | WO-2017093397 A1 * | 6/2017 | ............ A23L 33/105 |
| WO | WO-2017129640 A1 * | 8/2017 | .............. A23L 33/21 |

OTHER PUBLICATIONS

Comparison of Growth of Healthy Term Infants Fed Extensively Hydrolyzed Protein- and Amino Acid-Based Infant Formulas Marlene W. Borschel (Year: 2018).*
Chinese Office Action for Appl No. 202080083286.8 dated Jul. 20, 2023.
Holvoet et al., "Impact of Consumption of the Human Milk Oligosaccharides 2'-FL and LNnT on Reduction of Risk of Allergic Sensitisation", Food and Agricultural Immunology, vol. 35, Issue No. 1, 2024, pp. 1-20.
European Office Action for Appl No. 20 841 726.1-1105 dated Aug. 2, 2024, 6 pages.
Li et al. "Microbial Composition and In Vitro Fermentation Patterns of Human Milk Oligosaccharides and Prebiotics Differ between Formula-Fed and Sow-Reared Piglets" The Journal of Nutrition, 2012, vol. 142, pp. 681-689.
Castanys-Munoz et al. "2'-fucosyllactose: an abundant, genetically determined soluble glycan present in human milk" Nutrition Reviews, 2013, vol. 71, No. 12, pp. 773-789.
Haczku et al., "Aspergillus Fumigatus-Induced Allergic Airway Inflammation Alters Surfactant Homeostasis and Lung Function in BALB/c Mice", American Journal of Respiratory Cell and Molecular Biology, vol. 25, Issue No. 1, 2001, pp. 45-50.
Singh et al., "Dietary Polyphenols in the Prevention and Treatment of Allergic Diseases", Clinical & Experimental Allergy, vol. 41, Issue No. 10, 2011, pp. 1-14.
Chinese Office Action for Appl No. 202080083286.8 dated Jan. 4, 2024.
Nowak-Wegrzyn et al., "Confirmed Hypoallergenicity of a Novel Whey-Based Extensively Hydrolyzed Infant Formula Containing Two Human Milk Oligosaccharides", Nutrients, vol. 11, Issue No. 07, 2019, pp. 1-10.
Japanese Office Action for Appl No. 2022-535226 dated Dec. 17, 2024, 5 pages.

* cited by examiner

*Primary Examiner* — Jyoti Chawla
(74) *Attorney, Agent, or Firm* — K&L Gates LLP

(57) ABSTRACT

An infant formula for use in preventing or reducing the occurrence of allergic sensitisation in an infant, wherein the infant formula comprises 0.8-2.5 g/L 2'-fucosyllactose (2'FL) and/or 0.05-0.2 g/L lacto-N-neotetraose (LNnT).

14 Claims, 3 Drawing Sheets

INFANT FORMULA

CROSS REFERENCE TO RELATED APPLICATIONS

The present application is a National Stage of International Application No. PCT/EP2020/087901, filed on Dec. 28, 2020, which claims priority to European Patent Application No. 19219957.8, filed on Dec. 30, 2019, the entire contents of which are being incorporated herein by reference.

FIELD OF THE INVENTION

The present invention relates to infant formulas for use in preventing or reducing the occurrence of allergic sensitisation in an infant. In particular, the invention relates to infant formulas comprising 2'-fucosyllactose (2'FL) and/or lacto-N-neotetraose (LNnT).

BACKGROUND TO THE INVENTION

The incidence of allergic diseases such as atopic dermatitis, food allergy and asthma is increasing globally. For example, 300 million people worldwide suffer from asthma, and in the European Union 11-26 million people have a food allergy (Martins, T. B. et al. (2014) J Allergy Clin Immunol 133: 589-91).

There is growing evidence regarding the role of infant gut microbial composition in the immune trajectory and allergy development of the infant host (Quante M. et al. (2012) BMC Public Health 12: 1021). As such, environmental factors such as diet, pollution, urban lifestyle, cleanliness and birth method have been associated with the development of the immune system and allergic diseases (Seppo, A. E. et al. (2017) J Allergy Clin Immunol 139: 708-11 e5; Azad, M. B. et al. (2018) J Nutr 148: 1733-42).

Breast milk is an immunologically active fluid, which contains a host of components that may modulate the development of the immune system and, in turn, the development of allergic disease. The influence of human milk oligosaccharides (HMOs), the third most abundant component in breast milk, in the development of allergic disease has been of particular interest. HMOs are structurally varied lactose-based complex glycans that include both short- and long-chain oligosaccharides. The number (over 200 HMOs have been identified) and structural diversity of HMOs in human breast milk are not observed in other mammalian milks. HMO composition is influenced by both environmental and genetic influences and varies greatly across maternal populations. Synthesised in the mammary glands, HMO quantity in breast milk ranges from about 20.9 g/L in colostrum to 12.9 g/L in mature milk.

There is some in vitro evidence suggesting that HMOs may modulate the allergic response, and certain HMOs (e.g. 2'-fucosyllactose, 2'FL) have been suggested to decrease allergic response in a food allergy animal model. In addition, association studies have led to the identification of some breast milk levels of HMOs that correlate with milk or food allergy in infants. However, synthetic food grade HMOs have until recently been unavailable, which has rendered the testing of HMOs on infants in intervention studies impossible.

In addition, there has remained uncertainty over the identity of particular HMOs that may be beneficial in modulating allergy, and also the levels of the HMOs that may provide for a beneficial effect.

Human breast milk and breast feeding are considered to be the optimal form of nutrition for healthy infants during the first months of life. However, there is a need for nutritional sources that can be used in addition to breast milk. Furthermore, not all infants can be breast fed and the needs of more vulnerable infants, such as preterm infants, cannot be achieved by their mother's milk, so there is also a need for alternatives to breast milk. Nutritional compositions, such as infant formulas, that satisfy the nutritional requirements of infants may be used as a substitute for or complement to human breast milk. However, the composition of infant formulas must be carefully controlled to satisfy nutritional requirements, provide acceptable taste and further aid the development of infants, particularly when targeted to infants who are allergic or at risk of allergy.

Accordingly, there remains a significant need for nutritional compositions, such as infant formulas, that may be used to prevent or reduce the development of allergies in infants, in particular infant formulas that are effective in the prevention or reduction of allergic sensitisation in infants.

SUMMARY OF THE INVENTION

The present inventors have surprisingly found that intermediate levels of the HMOs 2'-fucosyllactose (2'FL) and lacto-N-neotetraose (LNnT) are most efficacious in the prevention of allergic sensitisation. The inventors have found that levels that are lower or higher than an optimal intermediate dose may be less beneficial.

The inventors analysed HMO levels in the breast milk from a cohort of mothers and identified two HMOs, 2'FL and LNnT, as associated with skin sensitisation or skin rash. In addition, from analysis of the distribution of the HMO levels in a clinically diagnosed population, the inventors found a non-lineal distribution suggesting a beneficial effect of intermediate dosing levels. The inventors then carried out animal model studies, which confirmed that intermediate levels of the HMOs indeed exhibit a more beneficial effect in the prevention of allergic sensitisation when compared to lower or higher doses.

Accordingly, in one aspect, the invention provides infant formula for use in preventing or reducing the occurrence of allergic sensitisation in an infant, wherein the infant formula comprises 0.8-2.5 g/L 2'-fucosyllactose (2'FL) and/or 0.05-0.2 g/L lacto-N-neotetraose (LNnT).

In another aspect, the invention provides a method for preventing or reducing the occurrence of allergic sensitisation in an infant, wherein the method comprises administering to the infant an infant formula, wherein the infant formula comprises 0.8-2.5 g/L 2'-fucosyllactose (2'FL) and/or 0.05-0.2 g/L lacto-N-neotetraose (LNnT).

In some embodiments, the infant formula comprises 0.8-1.5 g/L, 0.8-1.4 g/L, 0.8-1.3 g/L, 0.8-1.2 g/L, 0.8-1.1 g/L, 0.9-1.1 g/L, or about 1 g/L 2'FL. In some embodiments, the infant formula comprises 0.8-1.2 g/L 2'FL. In some embodiments, the infant formula comprises 0.9-1.1 g/L 2'FL.

In some embodiments, the infant formula comprises 1-1.5 g/L, 1-1.4 g/L, 1-1.3 g/L, 1-1.2 g/L, 1-1.1 g/L, or about 1 g/L 2'FL. In some embodiments, the infant formula comprises 1-1.1 g/L 2'FL.

In preferred embodiments, the infant formula comprises about 1 g/L 2'FL.

In some embodiments, the infant formula comprises 1.5-2.5 g/L, 1.5-2.4 g/L, 1.5-2.3 g/L, 1.5-2.2 g/L, 1.5-2.1 g/L, 1.5-2 g/L, 1.6-2 g/L, 1.7-1.9 g/L, or about 1.8 g/L 2'FL. In some embodiments, the infant formula comprises 1.5-2 g/L 2'FL. In some embodiments, the infant formula comprises 1.7-1.9 g/L 2'FL.

In preferred embodiments, the infant formula comprises about 1.8 g/L 2'FL.

In some embodiments, the infant formula comprises 0.05-0.15 g/L, 0.06-0.14 g/L, 0.07-0.13 g/L, 0.08-0.12 g/L, 0.09-0.11 g/L or about 0.1 g/L LNnT. In some embodiments, the infant formula comprises 0.08-0.12 g/L LNnT. In some embodiments, the infant formula comprises 0.09-0.11 g/L LNnT.

In preferred embodiments, the infant formula comprises about 0.1 g/L LNnT.

In preferred embodiments, the infant formula comprises 2'FL and LNnT.

In some embodiments, the infant formula comprises about 1.5-2 g/L 2'FL and about 0.08-0.12 g/L LNnT. In some embodiments, the infant formula comprises about 1.7-1.9 g/L 2'FL and about 0.09-0.11 g/L LNnT. In some embodiments, the infant formula comprises about 1.8 g/L 2'FL and about 0.1 g/L LNnT.

In some embodiments, the infant formula is an extensively hydrolysed infant formula (eHF). In some embodiments, the infant formula is an amino acid-based infant formula (AAF).

In preferred embodiments, the infant formula comprises protein, carbohydrate and fat.

In some embodiments, the infant formula comprises:
 (a) 1.8-3.2 g protein per 100 kcal;
 (b) 9-14 g carbohydrate per 100 kcal; and/or
 (c) 4.0-6.0 g fat per 100 kcal.

In some embodiments, the infant formula comprises about 2.4 g or less protein per 100 kcal.

In some embodiments, the infant formula comprises 1.8-2.4 g protein per 100 kcal, 2.1-2.3 g protein per 100 kcal, or 2.15-2.25 g protein per 100 kcal. In preferred embodiments, the infant formula comprises about 2.2 g protein per 100 kcal.

In some embodiments, about 30% or less by weight of the fat is medium chain triglycerides (MCTs).

In some embodiments, about 25% or less by weight, 20% or less by weight, 15% or less by weight, 10% or less by weight, 5% or less by weight, or 1% or less by weight of the fat in the infant formula is medium chain triglycerides (MCTs).

In some embodiments, the infant formula comprises no added MCTs.

In another aspect, the invention provides an infant formula comprising 0.05-0.2 g/L, 0.05-0.15 g/L, 0.05-0.1 g/L or about 0.1 g/L LNnT, preferably wherein the infant formula comprises about 0.1 g/L LNnT.

Figure 1:
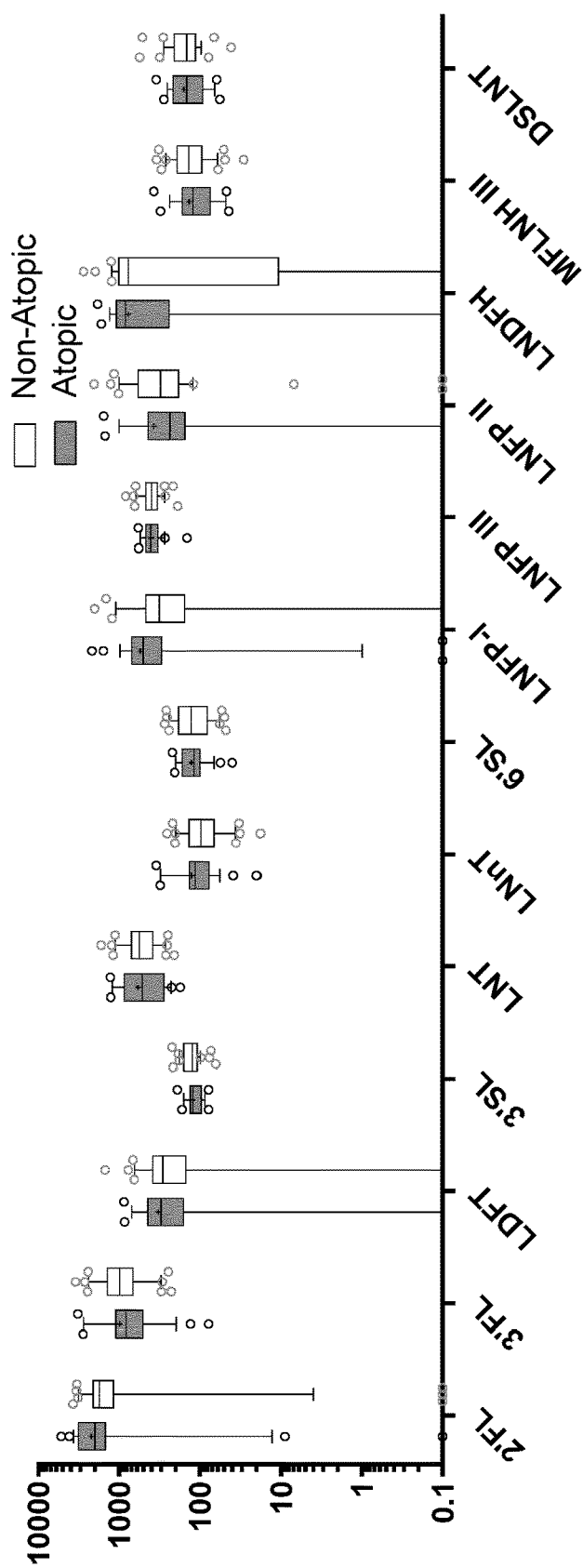
FIG. 1

Human milk oligosaccharide (HMO) levels in breast milk of mothers from non-allergic (N=40) and medically diagnosed allergic/atopic infants (N=29). Milk samples were taken at 3 months. The box plots show the median (horizontal line) within the box indicating the 25th and 75th percentiles, the whiskers indicate the 10th and 90th percentile, and circles represent upper and lower 10%. No statistical differences (Q or corrected p>0.05) between HMOs from the milk of the non-allergic and allergic groups were found (non-parametric Mann-Whitney-Wilcoxon test).

FIG. 2

Quartile analysis of (A) 2'-fucosyllactose (2'FL) levels (mg/L); and (B) lacto-N-neotetraose (LNnT) (μg/mL) in human breast milk showing differences in distributions between population sub-groups: percent values in green (highlighted with an oval) show statistically significant positive results; and percent values in red (highlighted with a rectangle) show negative results.

FIG. 3

Optimal intermediate dosing at 1% of a 2:1 mix of the 2'FL and LNnT (HMO) in the prevention of allergic sensitisation as shown by reduced specific IgG concentrations observed in a mouse model of skin sensitisation.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Infant Formula

The term "infant formula" may refer to a foodstuff intended for particular nutritional use by infants during the first year of life and satisfying by itself the nutritional requirements of this category of person, as defined in European Commission Regulation (EU) 2016/127 of 25 Sep. 2015.

In some embodiments, the infant formula is an extensively hydrolysed infant formula (eHF).

In some embodiment the infant formula is a 100% whey based partially hydrolysed formula (pHF), In some embodiments, the infant formula is an amino acid-based infant formula (AAF).

In some embodiments, the formulation is a supplement, that can be mixed into e.g. an infant formula, or meal, that does not contain HMOs.

The term "extensively hydrolysed infant formula" or "eHF" may refer to an infant formula comprising extensively hydrolysed protein. The eHF may be a hypoallergenic infant formula which provides complete nutrition for infants who cannot digest intact cow's milk protein (CMP) or who are intolerant or allergic to CMP.

The term "amino acid-based infant formula" or "AAF" may refer to an infant formula comprising only free amino acids as a protein source. The AAF may contain no detectable peptides. The AAF may be a hypoallergenic infant formula which provides complete nutrition for infants with food protein allergy and/or food protein intolerance. For example, the AAF may be a hypoallergenic infant formula which provides complete nutrition for infants who cannot digest intact CMP or who are intolerant or allergic to CMP, and who may have extremely severe or life-threatening symptoms and/or sensitisation against multiple foods.

A "hypoallergenic" composition is a composition which is unlikely to cause allergic reactions. Suitably, the infant formula of the invention is tolerated by more than 90% of infants with cow's milk protein allergy (CMPA). This is in line with the guidance provided by the American Academy of Pediatrics (Committee on Nutrition (2000) Pediatrics 106(2): 346-349). Suitably, the infant formula of the invention may not contain peptides which are recognised by CMP-specific IgE, e.g. IgE from subjects with CMPA.

A pHF composition is a composition which is hydrolysed to reduce exposure the the intact milk allergen. Suitably, the infant formula of the invention is intended for general infant population for the prevention of allergic diseases.

Infants can be fed solely with the infant formula or the infant formula can be used as a complement of human milk.

The infant formula of the invention may be in the form of a powder or liquid.

The liquid may be, for example, a concentrated liquid infant formula or a ready-to-feed infant formula. The infant formula may be in the form of a reconstituted infant formula (i.e. a liquid infant formula that has been reconstituted from a powdered form). The concentrated liquid infant formula is preferably capable of being diluted into a liquid composition suitable for feeding an infant, for example by the addition of water.

In some embodiments, the infant formula is in a powdered form. The powder is capable of being reconstituted into a liquid composition suitable for feeding an infant, for example by the addition of water.

The infant formula may have an energy density of about 60-72 kcal per 100 mL, when formulated as instructed. Suitably, the infant formula may have an energy density of about 60-70 kcal per 100 mL, when formulated as instructed.

Human Milk Oligosaccharides

The infant formula of the invention contains at least one of the human milk oligosaccharides (HMOs) 2'-fucosyllactose (2'FL) and/or lacto-N-neotetraose (LNnT).

Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk. Almost all HMOs have a lactose moiety at their reducing end while sialic acid and/or fucose (when present) occupy terminal positions at the non-reducing ends. HMOs can be acidic (e.g. charged sialic acid containing oligosaccharides) or neutral (e.g. fucosylated oligosaccharides).

The infant formula of the invention comprises 2'-fucosyllactose (2'FL) and/or lacto-N-neotetraose (LNnT).

In some embodiments, the infant formula comprises 2'FL. In some embodiments, there is no other type of fucosylated oligosaccharide than 2'FL, i.e. the infant formula of the invention comprises only 2'FL as fucosylated oligosaccharide.

The 2'FL may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Alternatively, 2'FL may be produced by chemical synthesis from lactose and free fucose.

In some embodiments, the infant formula comprises LNnT. In some embodiments, there is no other type of N-acetylated oligosaccharide than LNnT, i.e. the infant formula of the invention comprises only LNnT as N-acetylated oligosaccharide.

The LNnT may be synthesised chemically by enzymatic transfer of saccharide units from donor moieties to acceptor moieties using glycosyltransferases as described, for example, in U.S. Pat. No. 5,288,637 and WO 1996/010086. Alternatively, LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M. and Stutz, A. E. (1999) Angew. Chem. Int. Ed. 38: 827-828. N-acetyl-lactosamine produced in this way may then be transferred to lactose as the acceptor moiety.

In some embodiments, the infant formula comprises an oligosaccharide mixture that comprises 2'FL and/or LNnT. In preferred embodiments, the infant formula comprises an oligosaccharide mixture that consists of 2'FL and LNnT. The infant formula of the invention may, for example, comprise only 2'FL as fucosylated oligosaccharide and only LNnT as N-acetylated oligosaccharide.

2'FL may, for example, be present in the infant formula in a total amount of 0.8-2.5 g/L of the infant formula (when formulated as instructed).

In some embodiments, the infant formula comprises (when formulated as instructed) 0.8-1.5 g/L, 0.8-1.4 g/L, 0.8-1.3 g/L, 0.8-1.2 g/L, 0.8-1.1 g/L, 0.9-1.1 g/L, or about 1 g/L 2'FL. In some embodiments, the infant formula comprises (when formulated as instructed) 0.8-1.2 g/L 2'FL. In some embodiments, the infant formula comprises (when formulated as instructed) 0.9-1.1 g/L 2'FL.

In some embodiments, the infant formula comprises (when formulated as instructed) 1-1.5 g/L, 1-1.4 g/L, 1-1.3 g/L, 1-1.2 g/L, 1-1.1 g/L, or about 1 g/L 2'FL. In some embodiments, the infant formula comprises (when formulated as instructed) 1-1.1 g/L 2'FL.

In preferred embodiments, the infant formula comprises (when formulated as instructed) about 1 g/L 2'FL.

In some embodiments, the infant formula comprises (when formulated as instructed) 1.5-2.5 g/L, 1.5-2.4 g/L, 1.5-2.3 g/L, 1.5-2.2 g/L, 1.5-2.1 g/L, 1.5-2 g/L, 1.6-2 g/L, 1.7-1.9 g/L, or about 1.8 g/L 2'FL. In some embodiments, the infant formula comprises (when formulated as instructed) 1.5-2 g/L 2'FL. In some embodiments, the infant formula comprises (when formulated as instructed) 1.7-1.9 g/L 2'FL.

In preferred embodiments, the infant formula comprises (when formulated as instructed) about 1.8 g/L 2'FL.

LNnT may, for example, be present in the infant formula in a total amount of 0.05-0.2 g/L of the infant formula (when formulated as instructed).

In some embodiments, the infant formula comprises (when formulated as instructed) 0.05-0.15 g/L, 0.06-0.14 g/L, 0.07-0.13 g/L, 0.08-0.12 g/L, 0.09-0.11 g/L or about 0.1 g/L LNnT. In some embodiments, the infant formula comprises (when formulated as instructed) 0.08-0.12 g/L LNnT. In some embodiments, the infant formula comprises (when formulated as instructed) 0.09-0.11 g/L LNnT.

In preferred embodiments, the infant formula comprises (when formulated as instructed) about 0.1 g/L LNnT.

In preferred embodiments, the infant formula comprises 2'FL and LNnT.

In some embodiments, the infant formula comprises (when formulated as instructed) about 0.8-1.2 g/L 2'FL and about 0.08-0.12 g/L LNnT.

In some embodiments, the infant formula comprises (when formulated as instructed) about 0.9-1.1 g/L 2'FL and about 0.09-0.11 g/L LNnT.

In some embodiments, the infant formula (when formulated as instructed) comprises about 1.8 g/L 2'FL and about 0.1 g/L LNnT.

In some embodiments, the infant formula comprises (when formulated as instructed) about 1.5-2 g/L 2'FL and about 0.08-0.12 g/L LNnT.

In some embodiments, the infant formula comprises (when formulated as instructed) about 1.7-1.9 g/L 2'FL and about 0.09-0.11 g/L LNnT.

In some embodiments, the infant formula (when formulated as instructed) comprises about 1.8 g/L 2'FL and about 0.1 g/L LNnT.

In some embodiments, the infant formula comprises (when formulated as instructed) 0.12-0.225 g/100 kcal, 0.12-0.21 g/100 kcal, 0.12-0.195 g/100 kcal, 0.12-0.18 g/100 kcal, 0.12-0.165 g/100 kcal, 0.135-0.165 g/100 kcal, or about 0.15 g/100 kcal 2'FL. In some embodiments, the infant formula comprises (when formulated as instructed) 0.12-0.18 g/100 kcal 2'FL. In some embodiments, the infant formula comprises (when formulated as instructed) 0.135-0.165 g/100 kcal 2'FL.

In some embodiments, the infant formula comprises (when formulated as instructed) 0.15-0.225 g/100 kcal, 0.15-0.21 g/100 kcal, 0.15-0.195 g/100 kcal, 0.15-0.18 g/100 kcal, 0.15-0.165 g/100 kcal, or about 0.15 g/100 kcal 2'FL. In some embodiments, the infant formula comprises (when formulated as instructed) 0.15-0.165 g/100 kcal 2'FL.

In preferred embodiments, the infant formula comprises (when formulated as instructed) about 0.15 g/100 kcal 2'FL.

In some embodiments, the infant formula comprises (when formulated as instructed) 0.225-0.375 g/100 kcal, 0.225-0.36 g/100 kcal, 0.225-0.345 g/100 kcal, 0.225-0.33 g/100 kcal, 0.225-0.315 g/100 kcal, 0.225-0.3 g/100 kcal, 0.24-0.3 g/100 kcal, 0.255-0.285 g/100 kcal, or about 0.27 g/100 kcal 2'FL. In some embodiments, the infant formula comprises (when formulated as instructed) 0.225-2 g/100 kcal 2'FL. In some embodiments, the infant formula comprises (when formulated as instructed) 0.255-0.285 g/100 kcal 2'FL.

In preferred embodiments, the infant formula comprises (when formulated as instructed) about 0.27 g/100 kcal 2'FL.

LNnT may, for example, be present in the infant formula in a total amount of 0.0075-0.03 g/100 kcal of the infant formula (when formulated as instructed).

In some embodiments, the infant formula comprises (when formulated as instructed) 0.0075-0.0225 g/100 kcal, 0.009-0.021 g/100 kcal, 0.0105-0.0195 g/100 kcal, 0.012-0.018 g/100 kcal, 0.0135-0.0165 g/100 kcal or about 0.015 g/100 kcal LNnT. In some embodiments, the infant formula comprises (when formulated as instructed) 0.012-0.018 g/100 kcal LNnT. In some embodiments, the infant formula comprises (when formulated as instructed) 0.0135-0.0165 g/100 kcal LNnT.

In preferred embodiments, the infant formula comprises (when formulated as instructed) about 0.015 g/100 kcal LNnT.

Protein

The term "protein" includes peptides and free amino acids. The protein content of the infant formula may be calculated by any method known to those of skill in the art. Suitably, the protein content may be determined by a nitrogen-to-protein conversion method. For example, as described in Maubois, J. L. and Lorient, D. (2016) Dairy Science & Technology 96(1): 15-25. Preferably the protein content is calculated as nitrogen content×6.25, as defined in European Commission Regulation (EU) 2016/127 of 25 Sep. 2015. The nitrogen content may be determined by any method known to those of skill in the art. For example, nitrogen content may be measured by the Kjeldahl method.

Protein Concentration

The protein content of the infant formula is preferably in the range 1.8-3.2 g protein per 100 kcal. In some embodiments, the protein content of the infant formula is in the range 1.8-2.8 g protein per 100 kcal.

eHFs typically contain 2.6-2.8 g protein per 100 kcal and AAFs typically contain 2.8-3.1 g protein per 100 kcal, for example to cover the needs of infants suffering gastrointestinal pathologies with severe malabsorption or infants requiring more proteins and calories to cover a higher metabolic rate.

Infant formulas, such as an eHF or an AAF, with a lower protein content may support appropriate growth and development of allergic infants, as well as being safe and well-tolerated.

Accordingly, in some embodiments, the infant formula may comprise about 2.4 g or less protein per 100 kcal. For example, the infant formula may comprise about 2.3 g or less protein per 100 kcal, 2.25 g or less protein per 100 kcal, or 2.2 g or less protein per 100 kcal.

Suitably, the infant formula comprises about 1.8 g or more protein per 100 kcal. For example, the infant formula may comprise about 1.86 g or more protein per 100 kcal, 1.9 g or more protein per 100 kcal, 2.0 g or more protein per 100 kcal, or 2.1 g or more protein per 100 kcal. Preferably, the infant formula comprises about 1.86 g or more protein per 100 kcal, in line with present EU regulations (EFSA NDA Panel (2014) EFSA journal 12(7): 3760).

In some embodiments, the infant formula may comprise 1.8-2.4 g protein per 100 kcal, 1.86-2.4 g protein per 100 kcal, 1.9-2.4 g protein per 100 kcal, 2.0-2.4 g protein per 100 kcal, 2.0-2.3 g protein per 100 kcal, 2.1-2.3 g protein per 100 kcal, or 2.15-2.25 g protein per 100 kcal.

Preferably, the infant formula comprises about 2.2 g protein per 100 kcal.

Protein Source

The source of protein may be any source suitable for use in an infant formula. Suitably, the protein is cow's milk protein.

In some embodiments, the infant formula does not comprise dairy protein. In some embodiments, the infant formula does not comprise cow's milk protein. Accordingly, in some embodiments 100% by weight of the total protein is non-dairy protein.

In some embodiments, the infant formula comprises plant protein. Example plant proteins that may optionally be used in the infant formula of the invention, include potato, pea, rice, *quinoa*, oat, sunflower or coconut proteins, or combinations thereof. Further example non-dairy proteins for use in the infant formula include algal protein or leaf protein.

An extensively hydrolysed/hydrolysed whey-based formula may be more palatable than an extensively hydrolysed/hydrolysed casein-based formula and/or the subject may only be sensitised to casein protein. Suitably, therefore, more than about 50%, more than about 60%, more than about 70%, more than about 80%, more than about 90%, or about 100% of the protein is whey protein. Preferably, the protein source is whey protein.

The whey protein may be a whey from cheese making, particularly a sweet whey such as that resulting from the coagulation of casein by rennet, an acidic whey from the coagulation of casein by an acid, or the acidifying ferments, or even a mixed whey resulting from coagulation by an acid and by rennet. This starting material may be whey that has been demineralised by ion exchange and/or by electrodialysis and is known as demineralised whey protein (DWP).

The source of the whey protein may be sweet whey from which the caseino-glycomacropeptide (CGMP) has been totally or partially removed. This is called modified sweet whey (MSW). Removal of the CGMP from sweet whey results in a protein material with threonine and trytophan contents that are closer to those of human milk. A process for removing CGMP from sweet whey is described in EP880902.

The whey protein may be a mix of DWP and MSW.

In some embodiments, the amount of casein in the infant formula is undetectable, for example less than 0.2 mg/kg. The amount of casein may be determined by any method known to those of skill in the art.

Degree of Hydrolysis

In eHFs, the protein is "extensively hydrolysed", such that the eHFs may be tolerated by more than 90% of infants with CMPA.

Protein hydrolysates may have an extent of hydrolysis that is characterised by NPN/TN %, which refers to the non-protein nitrogen divided by the total nitrogen×100. The non-protein nitrogen refers to amino nitrogen that is free to react with a reagent such as trinitrobenzenesulfonic acid (TNBS). NPN/TN % may be determined by any method known to those of skill in the art. For example, NPN/TN % may be measured as described in Adler-Nissen (Adler-Nissen, J. (1979) J. Agric. Food Chem. 27: 1256-1262). Suitably, the protein may have an NPN/TN % greater than 90%, greater than 95% or greater than 98%.

The extent of hydrolysis may also be determined by the degree of hydrolysis. The "degree of hydrolysis" (DH) is defined as the proportion of cleaved peptide bonds in a protein hydrolysate and may be determined by any method known to those of skill in the art. Suitably the degree of hydrolysis is determined by pH-stat, trinitrobenzenesulfonic acid (TNBS), o-phthaldialdehyde (OPA), trichloroacetic acid soluble nitrogen (SN-TCA), or formol titration methods. (Rutherfurd, S. M. (2010) Journal of AOAC International 93(5): 1515-1522). The degree of hydrolysis (DH) of the protein can, for example, be more than 90, more than 95 or more than 98.

The extent of hydrolysis may also be determined by the peptide molecular mass distribution. The peptide molecular mass distribution may be determined by high performance size exclusion chromatography, optionally with UV detection (HPSEC/UV) (Johns, P. W. et al. (2011) Food chemistry 125(3): 1041-1050). For example, the peptide molecular mass distribution may be a HPSEC peak area-based estimate determined at 205 nm, 214 nm or 220 nm. Suitably when the peptide molecular mass distribution is determined by HPSEC/UV, the "percentage of peptides by weight" that have a certain molecular mass may be estimated by the "fraction of peak area as a percentage of total peak area", that have the molecular mass, determined at 205 nm, 214 nm or 220 nm. Suitably, the extent of hydrolysis may be determined by the methods described in WO 2016/156077. Alternatively, the peptide molecular mass distribution may be determined by any method known to those of skill in the art, for example by sodium dodecyl sulphate-polyacrylamide gel electrophoresis (SDS-PAGE) (Chauveau, A. et al. (2016) Pediatric Allergy and Immunology 27(5): 541-543).

Theoretically, to bind with cell membrane-bound IgE, peptides should be greater than about 1500 Da in size (approximately 15 amino acids) and to crosslink IgE molecules and to induce an immune response, they must be greater than about 3000 Da in size (approximately 30 amino acids) (Nutten (2018) EMJ Allergy Immunol 3(1): 50-59).

Suitably, therefore, at least about 95%, at least about 98%, at least about 99% or about 100% of the peptides by weight in the eHF have a molecular mass of less than about 3000 Da. There may, for example, be no detectable peptides about 3000 Da or greater in size in the eHF.

Suitably, therefore, at least about 95%, at least about 98%, at least about 99% or about 100% of the peptides by weight in the eHF have a molecular mass of less than about 1500 Da. Preferably, at least 99% of the peptides by weight have a molecular mass of less than about 1500 Da. There may, for example, be no detectable peptides about 1500 Da or greater in size in the eHF.

Preferably, at least about 85%, at least about 90%, at least about 95%, at least about 98% or at least about 99% of the peptides by weight in the eHF have a molecular mass of less than about 1200 Da. More preferably, at least 95% or 98% of the peptides by weight in the eHF have a molecular mass of less than about 1200 Da.

Suitably, at least about 80%, at least about 85%, at least about 90%, or at least about 95% of the peptides by weight in the eHF have a molecular mass of less than about 1000 Da.

Preferably, at least about 95% of the peptides by weight in the eHF have a molecular mass of less than about 1000 Da.

Preferably, the eHF has no detectable peptides about 3000 Da or greater in size; and at least about 95% of the peptides by weight have a molecular mass of less than about 1200 Da.

Having a high proportion of di- and tri-peptides may improve nitrogen (protein) absorption, even in patients with gut impairment. PEPT1 is a dedicated facilitator transport route for small peptide absorption (e.g. di- and tri-peptides). In the first weeks of life, intestinal PEPT1 is important for nutritional intake, and later for diet transition following weaning.

Thus, at least about 30%, at least about 40%, or at least about 50% of the peptides by weight in the eHF may, for example, be di- and tri-peptides. Preferably, at least about 45%, at least about 50%, 45-55%, or 50-54% of the peptides by weight in the eHF are di- and tri-peptides. More preferably, about 51-53%, or most preferably, about 52% of the peptides by weight in the eHF are di- and tri-peptides.

Suitably, at least about 30%, at least about 40%, or at least about 50% of the peptides by weight in the eHF have a molecular mass of between 240 and 600 Da. Preferably, at least about 45%, at least about 50%, 45-55%, or 50-54% of the peptides by weight in the eHF have a molecular mass of between 240 and 600 Da. More preferably, about 51-53%, or most preferably, about 52% of the peptides by weight in the eHF have a molecular mass of between 240 and 600 Da.

The peptides in the eHF may, for example, have a median molecular weight of 300 Da to 370 Da, preferably 320 Da to 360 Da.

The principal recognised cow's milk allergens are alpha-lactalbumin (aLA), beta-lactoglobulin (bLG) and bovine serum albumin (BSA).

Suitably, therefore, the eHF may have non-detectable aLA content, for example about 0.010 mg/kg aLA or less; the eHF may have non-detectable bLG content, for example about 0.010 mg/kg bLG or less; and/or the eHF may have non-detectable BSA content, for example about 0.010 mg/kg BSA or less. Preferably, the eHF comprises no detectable amounts of aLA, bLG and BSA. The content of aLA, bLG and BSA may be determined by any method known to those of skill in the art, for example ELISA.

In preferred embodiments, the eHF of the present invention: has no detectable peptides about 3000 Da or greater in size; at least about 95% of the peptides by weight have a molecular mass of less than about 1200 Da; optionally at least about 45%, at least about 50%, or 45-55% of the peptides by weight have a molecular mass of between 240 and 600 Da and/or are di- or tri-peptides; and the eHF comprises no added MCT.

Method of Hydrolysis

Proteins for use in the infant formula of the invention may be hydrolysed by any suitable method known in the art. For example, proteins may be enzymatically hydrolysed, for example using a protease. For example, protein may be hydrolysed using alcalase (e.g. at an enzyme:substrate ratio of about 1-15% by weight and for a duration of about 1-10 hours). The temperature may range from about 40° C. to 60° C., for example about 55° C. The reaction time may be, for example, from 1 to 10 hours and pH values before starting hydrolysis may, for example, fall within the range 6 to 9, preferably 6.5 to 8.5, more preferably 7.0 to 8.0.

Porcine enzymes, in particular porcine pancreatic enzymes may be used in the hydrolysis process. For example, WO1993004593A1 discloses a hydrolysis process using trypsin and chymotrypsin, which includes a two-step hydrolysis reaction with a heat denaturation step in between to ensure that the final hydrolysate is substantially free of intact allergenic proteins. The trypsin and chymotrypsin used in these methods are preparations produced by extraction of porcine pancreas.

WO2016156077A1 discloses a process for preparing a milk protein hydrolysate comprising hydrolysing a milk-based proteinaceous material with a microbial alkaline serine protease in combination with bromelain, a protease from *Aspergillus* and a protease from *Bacillus*.

Free Amino Acids

The infant formula of the invention may comprise free amino acids.

The levels of free amino acids may be chosen to provide an amino acid profile that is sufficient for infant nutrition, in particular an amino acid profile that satisfies nutritional regulations (e.g. European Commission Directive 2006/141/EC).

Free amino acids may, for example, be incorporated in the eHF of the invention to supplement the amino acids comprised in the peptides.

Example free amino acids for use in the infant formula of the invention include histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof.

Free amino acids provide a protein equivalent source (i.e. contribute to the nitrogen content). As described above, having a high proportion of di- and tri-peptides may improve nitrogen (protein) absorption, even in patients with gut impairment. Accordingly, having a low proportion of free amino acids may also improve nitrogen (protein) absorption, even in patients with gut impairment.

Suitably, therefore, the free amino acids in the eHF may be present in a concentration of 50% or less, 40% or less, 30% or less, or 25% or less by weight based on the total weight of amino acids. Preferably, the eHF comprises 25% or less by weight of free amino acids based on the total weight of amino acids. More preferably, the free amino acids in the eHF are present in a concentration of 20-25%, 21-23%, or about 22% by weight based on the total weight of amino acids.

The free amino acids content may be determined by any method known of skill in the art. Suitably, the free amino acids content may be obtained by separation of the free amino acids present in an aqueous sample extract by ion exchange chromatography and photometric detection after post-column derivatisation with ninhydrin reagent. Total amino acids content may be obtained by hydrolysis of the test portion in 6 mol/L HCl under nitrogen and separation of individual amino acids by ion-exchange chromatography, as describe above.

In preferred embodiments, the eHF of the present invention: has no detectable peptides about 3000 Da or greater in size; at least about 95% of the peptides by weight have a molecular mass of less than about 1200 Da; optionally at least about 45%, at least about 50%, or 45-55% of the peptides by weight have a molecular mass of between 240 and 600 Da and/or are di- or tri-peptides, and/or 20-25%, 21-23%, or about 22% by weight based on the total weight of amino acids; and the eHF comprises no added MCT.

Carbohydrate

The carbohydrate content of the infant formula of the invention is preferably in the range 9-14 g carbohydrate per 100 kcal.

The carbohydrate may be any carbohydrate which is suitable for use in an infant formula.

Example carbohydrates for use in the infant formula of the invention include lactose, saccharose, maltodextrin and starch. Mixtures of carbohydrates may be used.

In some embodiments, the carbohydrate content comprises maltodextrin. In some embodiments, at least about 20%, at least about 25%, at least about 30%, at least about 35%, at least about 40%, at least about 50%, at least about 60% or at least about 70% by weight of the total carbohydrate content is maltodextrin.

In some embodiments, the carbohydrate content comprises lactose. In some embodiments, at least about 20%, at least about 25%, at least about 30%, at least about 35%, at least about 40%, at least about 50%, at least about 60% or at least about 70% by weight of the total carbohydrate content is lactose.

In some embodiments, the carbohydrate comprises lactose and maltodextrin.

Fat

The fat content of the infant formula of the invention is preferably in the range 4.0-6.0 g fat per 100 kcal.

The fat may be any lipid or fat which is suitable for use in an infant formula.

Example fats for use in the infant formula of the invention include sunflower oil, low erucic acid rapeseed oil, safflower oil, canola oil, olive oil, coconut oil, palm kernel oil, soybean oil, fish oil, palm oleic, high oleic sunflower oil and high oleic safflower oil, and microbial fermentation oil containing long chain, polyunsaturated fatty acids.

The fat may also be in the form of fractions derived from these oils, such as palm olein, medium chain triglycerides (MCT) and esters of fatty acids such as arachidonic acid, linoleic acid, palmitic acid, stearic acid, docosahexaeonic acid, linolenic acid, oleic acid, lauric acid, capric acid, caprylic acid, caproic acid, and the like.

Further example fats include structured lipids (i.e. lipids that are modified chemically or enzymatically in order to change their structure). Preferably, the structured lipids are sn2 structured lipids, for example comprising triglycerides having an elevated level of palmitic acid at the sn2 position of the triglyceride. Structured lipids may be added or may be omitted.

Oils containing high quantities of preformed arachidonic acid (ARA) and/or docosahexaenoic acid (DHA), such as fish oils or microbial oils, may be added.

Long chain polyunsaturated fatty acids, such as dihomo-γ-linolenic acid, arachidonic acid (ARA), eicosapentaenoic acid and docosahexaenoic acid (DHA), may also be added.

The infant formula may comprise 2-20 mg ARA per 100 kcal, 5-15 ARA per 100 kcal, or about 10 mg ARA per 100 kcal and/or 2-20 mg DHA per 100 kcal, 5-15 DHA per 100 kcal, or about 10 mg DHA per 100 kcal. Preferably, the infant formula comprises about 10 mg ARA per 100 kcal and about 10 mg DHA per 100 kcal.

Medium Chain Triglycerides (MCTs)

A high concentration of MCT may impair early weight gain. MCT is not stored and does not support fat storage. For instance, Borschel et al. have reported that infants fed formula without MCT gained significantly more weight between 1-56 days than infants fed formulas containing 50% of the fat from MCT (Borschel, M. et al. (2018) Nutrients 10(3): 289).

Thus, about 30% or less by weight of the fat may, for example, be medium chain triglycerides (MCTs) in the infant formula of the present invention.

In some embodiments, about 25% or less by weight, 20% or less by weight, 15% or less by weight, 10% or less by weight, 5% or less by weight, 4% or less by weight, 3% or less by weight, 2% or less by weight, 1% or less by weight, 0.5% or less by weight, or 0.1% or less by weight of the fat is medium chain triglycerides (MCTs).

In some embodiments, 0-30% by weight, 0-25% by weight, 0-20% by weight, 0-15% by weight, 0-10% by weight, 0-5% by weight, 0-4% by weight, 0-3% by weight, 0-2% by weight, 0-1% by weight, 0-0.5% by weight, or 0-0.1% by weight of the fat is medium chain triglycerides (MCTs).

Preferably, the infant formula comprises no added MCTs. Suitably, about 0% by weight of the fat is MCTs and/or the infant formula comprises no detectable MCTs. Suitably, the infant formula comprises no MCTs.

In preferred embodiments, the eHF of the present invention: has no detectable peptides about 3000 Da or greater in size; at least about 95% of the peptides by weight have a molecular mass of less than about 1200 Da; 45-55% of the peptides by weight have a molecular mass of between 240 and 600 Da; free amino acids are present in a concentration of 20-25% by weight based on the total weight of amino acid; and the eHF comprises no added MCT.

Further Ingredients

The infant formula of the invention preferably also contains all vitamins and minerals understood to be essential in the daily diet in nutritionally significant amounts. Minimum requirements have been established for certain vitamins and minerals.

Example vitamins, minerals and other nutrients for use in the infant formula of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine and L-carnitine. Minerals are usually added in their salt form.

The infant formula of the invention may comprise one or more carotenoids.

The infant formula of the invention may also comprise at least one probiotic. The term "probiotic" refers to microbial cell preparations or components of microbial cells with beneficial effects on the health or well-being of the host. In particular, probiotics may improve gut barrier function.

Preferred probiotics are those which as a whole are safe, are L(+) lactic acid producing cultures and have acceptable shelf-life for products that are required to remain stable and effective for up to 24 months.

Examples of probiotic micro-organisms for use in the infant formula of the invention include yeasts, such as *Saccharomyces*, *Debaromyces*, *Candida*, *Pichia* and *Torulopsis*; and bacteria, such as the genera *Bifidobacterium*, *Bacteroides*, *Clostridium*, *Fusobacterium*, *Melissococcus*, *Propionibacterium*, *Streptococcus*, *Enterococcus*, *Lactococcus*, *Staphylococcus*, *Peptostrepococcus*, *Bacillus*, *Pediococcus*, *Micrococcus*, *Leuconostoc*, *Weissella*, *Aerococcus*, *Oenococcus* and *Lactobacillus*.

Specific examples of suitable probiotic microorganisms are: *Saccharomyces cereviseae*, *Bacillus coagulans*, *Bacillus licheniformis*, *Bacillus subtilis*, *Bifidobacterium bifidum*, *Bifidobacterium infantis*, *Bifidobacterium longum*, *Enterococcus faecium*, *Enterococcus faecalis*, *Lactobacillus acidophilus*, *Lactobacillus alimentarius*, *Lactobacillus casei* subsp. *casei*, *Lactobacillus casei Shirota*, *Lactobacillus curvatus*, *Lactobacillus delbruckii* subsp. *lactis*, *Lactobacillus farciminus*, *Lactobacillus gasseri*, *Lactobacillus helveticus*, *Lactobacillus johnsonii*, *Lactobacillus rhamnosus* (*Lactobacillus* GG), *Lactobacillus sake*, *Lactococcus lactis*, *Micrococcus varians*, *Pediococcus acidilactici*, *Pediococcus pentosaceus*, *Pediococcus acidilactici*, *Pediococcus halophilus*, *Streptococcus faecalis*, *Streptococcus thermophilus*, *Staphylococcus carnosus* and *Staphylococcus xylosus*.

The infant formula of the invention may also contain other substances which may have a beneficial effect such as prebiotics, lactoferrin, fibres, nucleotides, nucleosides, short chain fatty acids, e.g butyrate, and/or postbiotics and the like.

Reduced Occurrence and Prevention of Allergic Sensitisation

The term "allergy" refers to a hypersensitivity of the immune system to a substance which is normally tolerated (an allergen). The allergy may be an allergy detected by a medical doctor. Examples of allergic diseases include atopic dermatitis, eczema, food allergy, asthma and rhinitis Immunisation is part of the normal immune response, which in healthy individuals occurs when the immune system registers a substance as a threat. As a consequence, for example, B cells may then produce antibodies that bind that substance.

The term "allergic sensitisation" refers to sensitisation of the immune system to agents that are normally tolerated and which would typically be harmless in the absence of an allergic response (known as allergens, for example substances in food or pollen).

While not wishing to be bound by theory, when allergens enter a body, they may be captured and presented by antigen presenting cells to other cells of the immune system, in particular T cells. Following interaction between T cells and B cells, B cells may then produce allergen-specific antibodies (IgE). Subsequently, once released into the blood, IgE antibodies may bind to mast cells, as well as other immune cells such as basophils. Individuals who are sensitised may then develop an allergic reaction on re-exposure to the allergen.

Thus, allergic sensitisation may refer to a priming of the immune system to recognise allergens. Individuals who are sensitised in this way may then develop an allergic reaction on re-exposure to the allergen.

In some embodiments, allergic sensitisation in an infant may be characterised by a total IgE concentration greater than 35 kU/L at 6 months of age and/or 53 kU/L at 12 months of age (Martins, T. B. et al. (2014) J Allergy Clin Immunol 133(2): 589-91). In some embodiments, allergic sensitisation in an adult may be characterised a total IgE level greater than 127 KU/L. The skilled person is readily able to determine IgE concentrations in a sample from a subject, for example using ImmunoCAP Phadia technology as disclosed in the Examples.

The infant formula of the invention may be used to reduce the occurrence of allergic sensitisation in an infant and/or prevent allergic sensitisation in an infant.

As used herein, "reduce the occurrence" of allergic sensitisation means that the infant formula reduces the likelihood of allergic sensitisation.

As used herein, "prevent" allergic sensitisation means that the infant has not yet been sensitised, and the infant formula prevents allergic sensitisation.

The term "infant" refers to a child under the age of 12 months, for example a child between 0 and 6 months of age.

In some embodiments, the infant is at risk of developing one or more allergies. For example, the infant may belong to a family with a history of one or more allergies.

In one aspect the invention provides a method of preventing or reducing the occurrence of allergic sensitisation in an infant, comprising administering to the infant an infant formula of the invention.

Method of Manufacture

The infant formula of the invention may be prepared in any suitable manner.

For example, the infant formula may be prepared by blending together the protein source, the carbohydrate source and the fat source in appropriate proportions. If used, the further emulsifiers may be included at this point. The vitamins and minerals may be added at this point but vitamins are usually added later to avoid thermal degradation. Any lipophilic vitamins, emulsifiers and the like may be dissolved in the fat source prior to blending. Water, preferably water which has been subjected to reverse osmosis, may then be mixed in to form a liquid mixture. Commercially available liquefiers may be used to form the liquid mixture. The liquid mixture may then be homogenised.

The liquid mixture may then be thermally treated to reduce bacterial loads. This may be carried out, for example, by means of steam injection, or using an autoclave or heat exchanger, for example a plate heat exchanger.

The liquid mixture may then be cooled and/or homogenised. The pH and solid content of the homogenised mixture may be adjusted at this point.

The homogenised mixture may then be transferred to a suitable drying apparatus such as a spray dryer or freeze dryer and converted to powder. If a liquid infant formula is preferred, the homogenised mixture may be sterilised, then aseptically filled into a suitable container or may be first filled into a container and then retorted.

The skilled person will understand that they can combine all features of the invention disclosed herein without departing from the scope of the invention as disclosed.

Preferred features and embodiments of the invention will now be described by way of non-limiting examples.

EXAMPLES

Some studies have shown that specific components of breast milk, considered separately, are associated with disease status in the mother or the child using univariate analyses. However, recent analysis approaches to evaluate the relationship between breast milk HMO components independently have shown not association with allergy. Example 1 identify the specific doses of 2FL and LNnt necessary for allergic sensitization protection. Example 2 confirms in animals the need for a specific dose to protect against allergic sensitisation.

Example 1

In the present study, we aimed to understand the association between human milk oligosaccharides (HMOs) level and allergic sensitization in humans While we confirmed a non-significant association when doing univariate analysis, suggesting no linear association between the level of HMOs and the risk of allergic sensitization; we found that the HMOs 2'-fucosyllactose (2'FL) and lacto-N-neotetraose (LNnT) protect against allergic sensitisation, and that a bell-shaped effect is observed showing optimum protection at intermediate doses, while lower and higher doses may be less effective.

Materials AND METHODS

Breast Milk Analysis (German Cohort)

A cohort of 156 mother/infant pairs was sub-selected from samples from the Life Child study (Seppo, A. E. et al. (2017) J Allergy Clin Immunol 139(2): 708-11 e5). The selection of samples was based on the availability of breast milk samples at three months along with the completion of allergy questionnaires by mothers at any time during the study and/or for infants in the first year of life of the infant.

For the purpose of the study, maternal allergic sensitisation was defined by the total IgE level greater than 127 KU/L (Martins, T. B. et al. (2014) J Allergy Clin Immunol 133(2): 589-91) and allergy was defined as self-reported asthma, rhinitis, atopic dermatitis, eczema and/or allergic reactions to specific food (with vomit, nausea, diarrhea, exacerbation of eczema or asthma symptoms) in the mother. For the purpose of this study, infant allergic sensitisation was defined as a total IgE greater than 35 kU/L and 53 kU/L, at 6 and 12 months, respectively (Martins, T. B. et al. (2014) J Allergy Clin Immunol 133(2): 589-91), and allergy risk as a positive answer to the questions "did a doctor ever diagnose food allergy in your child", "did your child ever have eczema/atopic dermatitis" or "did your child suffer from recurrent rashes associated with pruritus during more than 15 days" at 3, 6 months or at one year. Mother and child total IgE was quantified using ImmunoCAP Phadia technology.

In this cohort, allergy and confounders such as socioeconomic status were obtained via various questionnaires. Confounders were identified based on available literature associating allergy and breast milk components and were chosen based on available data (delivery mode (delivery), child gender (gender), child weight at birth (weight), exclusively breastfeeding at 3 months (Breastfeed), socioeconomic status (ecoStatus) and number of siblings (siblings)). This cohort was used as an exploratory cohort. Breast milk was expressed, collected and stored at −80° C. from lactating mothers in the third month postpartum (Quante, M. et al. (2012) BMC Public Health 12: 1021). One mother/child pair was excluded due to too many missing values for the breast milk component levels (>50%). The study was designed in accordance with the Declaration of Helsinki and under the supervision of the Ethics Committee of the University of Leipzig (Reg. No. 264-10-19042010). The LIFE Child study is registered in ClinicalTrials.gov under the clinical trial number: NCT02550236 (Poulain, T. et al. (2017) European Journal of Epidemiology 32(2): 145-58).

Component Level Assessment

Liquid chromatography analysis was carried out, for which samples were centrifuged for 5 minutes at 10,000×g. Samples were subsequently analysed using an Ultimate 3000-RD UHPLC system which contained an RF-200 fluorimeter and a 2-way ten port high-pressure switching valve (Thermo Fisher Scientific, Waltham, USA). Samples were loaded onto Acquity BEH Glycan and VanGuard BEH amide columns (Waters Corporation, Milford, USA) with a guard column between the injector and ten port valve. The temperature of the columns was 55° C., and the flow rate was 0.5 mL/min. The reliability of the method was validated by spike reliability assessments with calibration curves being validated using the standard of the oligosaccharide in question and a maltotriose control.

In total, absolute concentrations of 21 HMOs were measured: 2'-Fucosyllactose (2'FL), 3-Fucosyllactose (3'FL), 3'-Sialyllactose (3'SL), 6'-Sialyllactose (6'SL), 3'-Galactosyl lactose (3'GL), 6'-Galactosyllactose (6'GL), Lacto-N-tetrose (LNT), Lacto-N-neotetraose (LNnT), Lacto-N-fucopentaose I (LNFP I), Lacto-N-fucopentaose II (LNFP II), Lacto-N-fucopentaose III (LNFP III), Lacto-N-fucopentaose V (LNFP V), Lacto-N-neofucopentaose (LNnFP), Lactodifucotetraose (LDF), Lacto-N-tetraose b (LST b), Lacto-N-tetraose(LST c), difucosyllacto-N-hexaose a (DFLNHa), disialyllacto-N-tetraose (DSLNT), monofucosyllacto-N-hexaose (MFLNH III), Lacto-N-neodifucohexaose (LNnDFH) and Lacto-N-difucohexaose (LNDFH 1).

Univariate Analysis

To test for association between HMOs and allergic sensitization or allergy, logistic regression and Chi-squared testing was completed comparing individual HMO levels against the incidence of atopic dermatitis. The sum of the 21 HMOs was also included in statistical analysis and classified as 'Total HMOs'.

For the statistical analysis, the following confounding variables were included in the model: gender, delivery mode, parental allergy, breast milk Se and Le status and pets in the home. The non-parametric Mann-Whitney-Wilcoxon test was used to compare the differences in the levels of individual HMOs between the allergic and non-allergic infants.

Results

Association Between HMO and Allergy in the German Cohort

Demographics of the study population at baseline are shown in Table 1.

TABLE 1

Discovery Cohort Summary Demographic Data

| Variable | N = 121 | |
| --- | --- | --- |
| | Number of infants | % of Total Population |
| Sensitisation and or Allergy | 31 | 25.6% |
| Atopic Dermatitis/Eczema | 20 | 16.5% |
| IgE mediated Food Allergy | 8 | 6.6% |
| IgE Sensitisation | 11 | 9% |
| Female | 59 | 48.8% |
| Male | 62 | 51.2% |
| Age (Months) | 3 | |
| Gestational Age (mean number of weeks) | 39.4 | |
| C Section Delivery | 18 | 14.9% |
| Vaginal Delivery | 102 | 84.3% |
| Allergic Parent | 71 | 58.7% |
| Has Siblings | 57 | 47.1% |
| Allergic Nuclear Family Member | 65 | 53.7% |
| Pets in Household | 39 | 32.2% |
| Se+, Le+ | 92 | 76.0% |
| Se+, Le− | 12 | 9.9% |
| Se−, Le+ | 15 | 12.4% |
| Se−, Le− | 2 | 1.7% |

TABLE 2

Discovery Cohort Summary Demographic Data by SA Status.

| | SA (n = 31) | | NSA (n = 90) | |
| --- | --- | --- | --- | --- |
| Variable | Number of infants | % of SA Population | Number of infants | % of NSA Population |
| Female | 13 | 41.9% | 46 | 51.1% |
| Male | 18 | 58.1% | 44 | 48.9% |
| Age (months) | | 3 | | |
| Gestational Age (mean number of weeks) | 39.7 | | 39.2 | |
| C Section Delivery | 2 | 6.5% | 16 | 17.8% |
| Vaginal Delivery | 29 | 93.5% | 73 | 81.1% |
| Allergic Parent | 19 | 61.3% | 52 | 57.8% |
| Has Siblings | 13 | 41.9% | 44 | 48.9% |
| Allergic Nuclear Family Member | 17 | 54.8% | 48 | 53.3% |
| Pets in Household | 14 | 45.2% | 25 | 27.8% |
| Se+, Le+ | 23 | 74.2% | 69 | 76.7% |
| Se+, Le− | 5 | 16.1% | 7 | 7.78% |
| Se−, Le+ | 2 | 6.45% | 12 | 13.3% |
| Se−, Le− | 0 | 0.0% | 2 | 2.22% |

A total of 21 HMO levels were measured and are presented in FIG. 1. Using only medically diagnosed and or sensitized infants, no significant association was found between any HMO levels and medically diagnosed allergic infants versus non-allergic infants. Q-values or corrected p-values for multiple testing were all above 0.05.

HMO Levels and Association with the Risk of Allergic Sensitisation and Skin Rash We then assessed the possibility that HMOs may be linked with allergic sensitisation. Since less than 30% of the population was analysed for sensitisation in our cohort, we expanded the analysis to include the infants with a positive sensitisation as well as those with an increased risk of sensitisation based on prolonged skin rash or eczema. When looking at the distribution of 2'FL and LNnT levels in this extended population, we found a non-lineal distribution suggesting that only specific doses of 2FL, LNnT may be associated with a decreased risk for for allergic sensitisation (FIG. 2) and higher dose are not protective.

Figure 2:
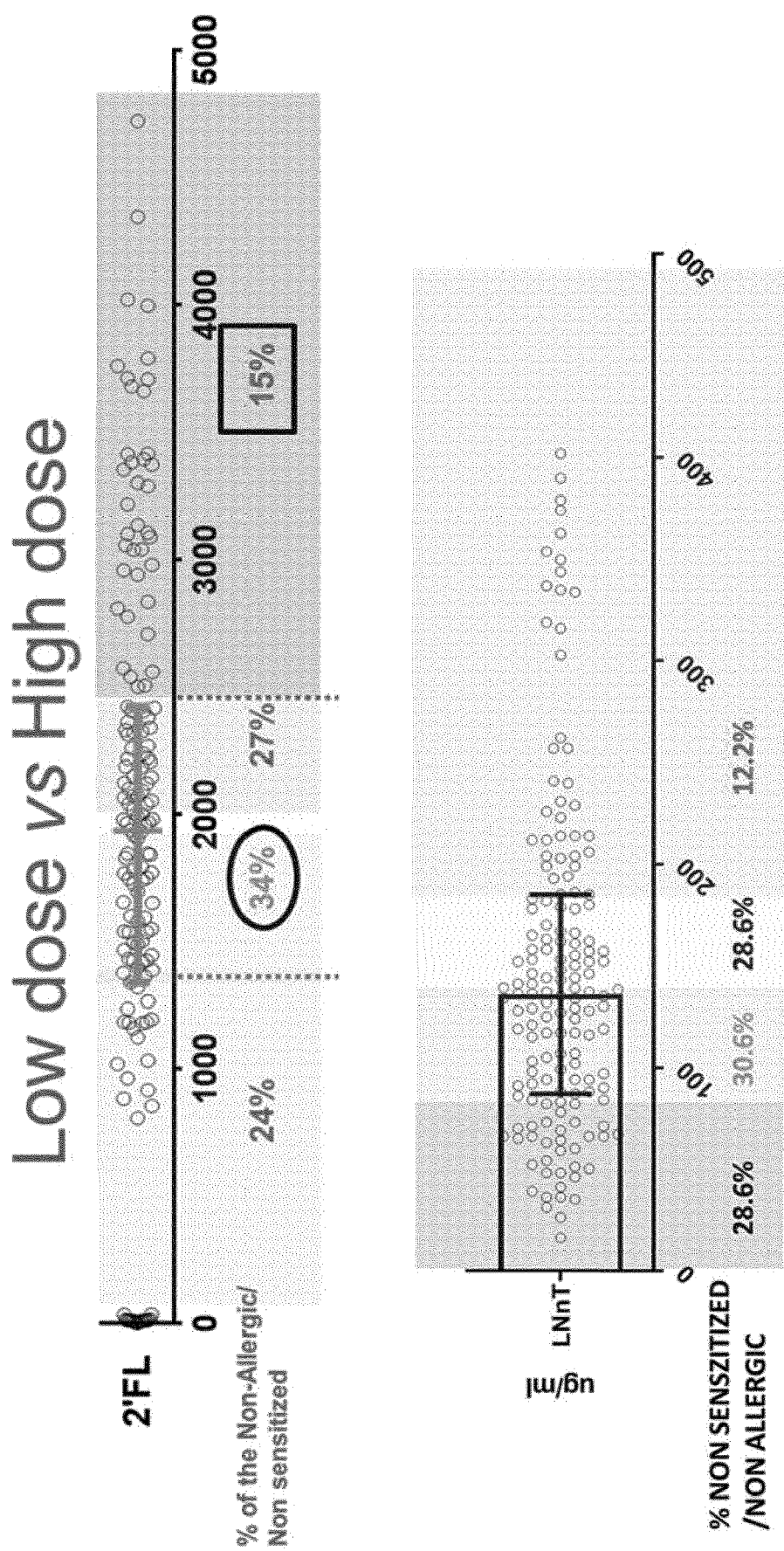

Quartile analysis of the population as shown in FIG. 2 identified levels of 2'FL and LNnT in breast milk that are associated with reducing allergic sensitisation: 2'FL levels in breast milk below 2.5 mg/L; and LNnT levels below 0.2 g/L appear to be associated with a particularly beneficial effect.

Example 2

In the present example, we aimed at confirming a bell shape effect of the protective effect of human milk oligosaccharides (HMOs) on allergy prevention in mice.

Preclinical Assays

The animal study protocol was approved by the Service Vétérinaire du Canton de Vaud, Switzerland. Briefly, 5 week-old female BALB/c mice were fed a diet supplemented with a HMO mixture of 2'FL and LNnT (2:1 weight ratio) at either 0%, 0.2%, 1%, 5% or 10% (by weight) starting at week 0 of the protocol. The backs of the mice were shaved and cleaned with 70% isopropanol solution (VWR; Nyon, Switzerland) and transepidermal water loss (TEWL) was measured as described below. During week 3, 100 μL of *Aspergillus fumigatus* (Af) protein extract (Greer Laboratories; Lenoir, N.C., USA) at 2 mg/mL (Sensitized group (S.)) or 100 μL of a 0.9% NaCl solution (nonsensitized group (N.S.); Merck; Zoug, Switzerland) was applied to a 1×1 cm patch of sterile gauze (Hartmann; Dermaplast, Chatenois, France) and secured to the skin with a bio-occlusive transparent dressing (Systagenix; Bioclusive, San Antonio, Tex., USA, Switzerland) and a Band-Aid (Mefix; Wasquehal, France). Subsequently, TEWL was again measured. After a 2-week resting period, a second, identical patch was applied for a further week and subsequently TEWL was again measured. Mice were then challenged intranasally with Af diluted in 0.9% NaCl. Mice were subsequently anaesthetised using isoflurane and euthanised after collecting blood from the abdominal aorta.

Specific IgG1 Quantification

Ninety-six well plates (Nunc Maxisorp; VWR) were coated overnight at 4° C. with Af protein extract (Greer Laboratories) at 50 µg/ml in carbonate buffer. Plates were then washed with PBS-0.05% Tween (Biorad, Reinach, Switzerland) and blocked with PBS-1% BSA (Sigma) for 1 h at 37° C. Diluted sera were incubated for 2 h at 37° C. After washing, plates were incubated 2 h at 37° C. with horseradish peroxidase (HRP)-conjugated goat anti-mouse IgG1- (Southern Biotech, Bioconcept Allschwil, Switzerland), and then with the HRP substrate tetramethylbenzidine (TMB) (KPL, Socochim, Lausanne, Switzerland). The reaction was stopped using 1 N hydrochloric acid (HCl, Merck). Absorbance was measured at 450 nm and the results expressed as optical density (OD) values.

Statistical Analysis

Statistical analysis was performed using JMP Pro 14 (SAS Software, Cary, USA). Figures were drawn with GraphPad Prism 6 (GraphPad Software, San Diego, USA). For all tests, a p-value of >0.05 was considered significant for the association.

For animal experimentation, the exact Wilcoxon non-parametric statistical test was used to compare groups. Statistical analyses were performed using the software R 2.14.1. Results with a p-value≤0.05 were considered as significant. Data are expressed as median±standard error (SE) of the median.

Beneficial Effects of HMOs on Allergic Sensitisation

To confirm that 2'FL and LnNT are able to protect against allergic sensitisation, we used an animal model to study the efficacy of a 2'FL:LNnT mix. Sensitisation of animals in a skin sensitisation mouse model was achieved epicutaneously using *Aspergillus fumigatus*.

Figure 3:
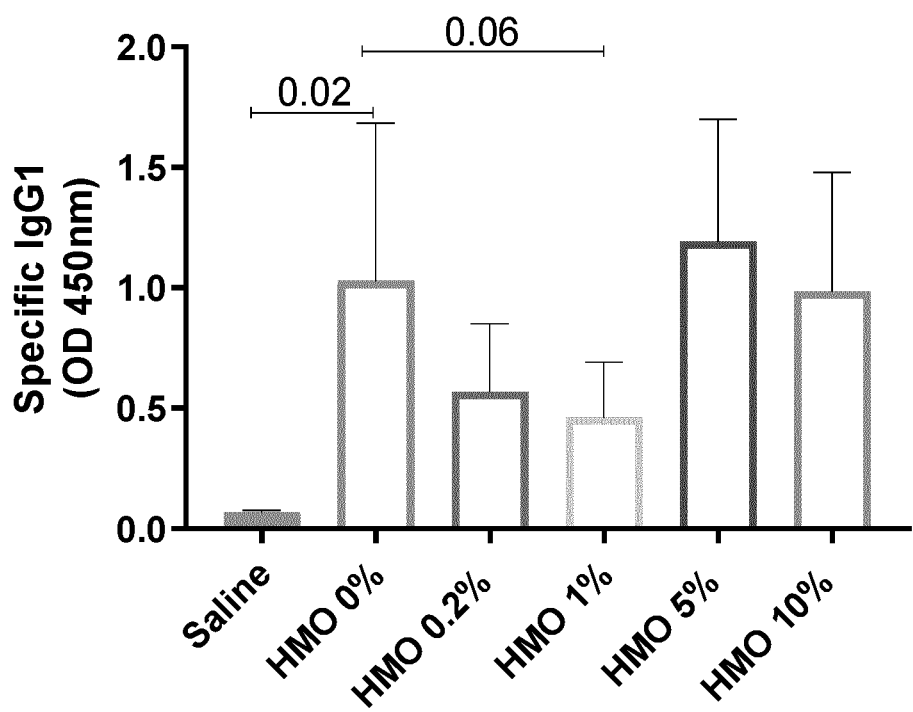

The variations in specific IgG with HMO level observed from these studies confirmed that the 2'FL and LNnT are particularly efficacious in preventing allergic sensitisation at the doses of 1% (in the mouse model of skin sensitisation, FIG. 3), while less efficacious at a lower or higher doses as shown by the bell-shaped curve.

DISCUSSION

We have shown that 2'FL and LNnT protect against allergic sensitisation and that a bell-shaped effect is observed showing improved protection at intermediate doses.

All publications mentioned in the above specification are herein incorporated by reference. Various modifications and variations of the disclosed uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method for preventing or reducing the occurrence of allergic sensitization in an infant comprising administering to the infant an infant formula, wherein the infant formula comprises 0.8-2.5 g/L 2'-fucosyllactose (2'FL) and 0.05-0.2 g/L lacto-N-neotetraose (LNnT), and comprising:
   (a) 1.8-3.2 g protein per 100 kcal;
   (b) 9-14 g carbohydrate per 100 kcal; and
   (c) 4.0-6.0 g fat per 100 kcal.

2. The method according to claim 1, wherein the infant formula comprises 2'FL in a concentration selected from the group consisting of 0.8-1.5 g/L, 1-1.5 g/L, or about 1 g/L.

3. The method according to claim 1, wherein the infant formula comprises 2'FL in a concentration selected from the group consisting of 1.5-2.5 g/L, 1.5-2 g/L, 1.6-2 g/L, or about 1.8 g/L.

4. The method according to claim 1, wherein the infant formula comprises LNnT in a concentration selected from the group consisting of 0.05-0.15 g/L or about 0.1 g/L.

5. The method according to claim 1, wherein the infant formula comprises 2'FL and LNnT.

6. The method according to claim 5, wherein the infant formula comprises about 1.8 g/L 2'FL and about 0.1 g/L LNnT.

7. The method according to claim 1, wherein the infant formula is an extensively hydrolysed infant formula (eHF) or an amino acid-based infant formula (AAF).

8. The method according to claim 1, wherein the infant formula comprises protein, carbohydrate and fat.

9. The method according to claim 1, wherein the infant formula comprises about 2.4 g or less protein per 100 kcal.

10. The method according to claim 1, wherein the infant formula comprises protein in a concentration selected from the group consisting of 1.8-2.4 g protein per 100 kcal, 2.1-2.3 g protein per 100 kcal, or 2.15-2.25 g protein per 100 kcal.

11. The method according to claim 1, wherein about 30% or less by weight of the fat is medium chain triglycerides (MCTs).

12. The method according to claim 1, wherein about 25% or less by weight of the fat in the infant formula is medium chain triglycerides (MCTs).

13. The method according to claim 1, wherein the infant formula comprises no added MCTs.

14. The method according to claim 1, wherein the infant has not yet been sensitised.

* * * * *